United States Patent
Sekkat

(10) Patent No.: US 8,445,457 B2
(45) Date of Patent: May 21, 2013

(54) ORAL PHARMACEUTICAL SOLUTIONS CONTAINING TELBIVUDINE

(75) Inventor: Nabila Sekkat, Basel (CH)

(73) Assignee: Novartis AG, Basel (CH)

( * ) Notice: Subject to any disclaimer, the term of this patent is extended or adjusted under 35 U.S.C. 154(b) by 314 days.

(21) Appl. No.: 12/667,975

(22) PCT Filed: Jul. 10, 2008

(86) PCT No.: PCT/EP2008/059016
§ 371 (c)(1),
(2), (4) Date: Jan. 6, 2010

(87) PCT Pub. No.: WO2009/007426
PCT Pub. Date: Jan. 15, 2009

(65) Prior Publication Data
US 2010/0197629 A1    Aug. 5, 2010

(30) Foreign Application Priority Data
Jul. 12, 2007  (EP) ................... 07112381

(51) Int. Cl.
*A01N 43/04*  (2006.01)
*A61K 31/70*  (2006.01)

(52) U.S. Cl.
USPC ............... 514/49; 514/43; 514/50; 514/51

(58) Field of Classification Search
None
See application file for complete search history.

(56) References Cited

U.S. PATENT DOCUMENTS

2004/0087541 A1    5/2004  Jonaitis et al.

FOREIGN PATENT DOCUMENTS

| WO | WO 95/27501  | 10/1995 |
| WO | WO 99/16447  | 4/1999  |
| WO | WO 9954312   | 10/1999 |
| WO | WO 9954326   | 10/1999 |
| WO | WO 03/037312 | 5/2003  |
| WO | WO 2004/012687 | 2/2004 |
| WO | WO 2006/130217 | 12/2006 |

OTHER PUBLICATIONS

Sorbera, L A et al.: "Telbivudine: Anti-HBV Agent", Drugs of the Future, Barcelona, ES, vol. 28, No. 9, 2003, pp. 870-879.
A satisfyingly sweet overview. (increasing use of nonnutritive sweeteners on food and beverages) *Prepared Foods* Mar. 1, 1997 | Bakal, Abraham.
A.I. Tichonov et al. Biopharmacija—Charkov: NFaU "Solotyje stranic", 2003, 241 pages: p. 141 table 5.1.
V.P. Georgijevsky (editor), Technologija I standartizacija lekarstv—Charkov: Co. Ltd. "RIREG", 1996, 784 pages; pp. 364-368, table 12.

*Primary Examiner* — Patrick Lewis
(74) *Attorney, Agent, or Firm* — David R. Kurlandsky

(57) ABSTRACT

A pharmaceutical solution suitable for oral administration comprising β-L-thymidine/2'-deoxy-L-thymidine (telbivudine), a pharmaceutically suitable solvent system, one or more taste-enhancing/masking agents, a preservative system, and a buffer system suitable to allow both drug stability and preservation.

15 Claims, No Drawings

ORAL PHARMACEUTICAL SOLUTIONS CONTAINING TELBIVUDINE

FIELD OF THE INVENTION

The present disclosure relates to pharmaceutical solutions suitable for oral administration comprising β-L-thymidine/2'-deoxy-L-thymidine (telbivudine), a pharmaceutically suitable solvent system, one or more taste-enhancing/masking agents, a preservative system, and a buffer system suitable to allow both drug stability and preservation. This application claims priority to EP application No. 07112381.4, filed 12 Jul. 2007, which is hereby incorporated by reference herein in its entirety.

BACKGROUND OF THE DISCLOSURE

β-L-Thymidine/2'-deoxy-L-thymidine (telbivudine) is described in *Coll Czech Chem Commun*, Vol. 37, pp. 4072 (1972)/*J Med Chem*, 35, p. 4214ff (1992). Further, β-L-thymidine/2'-deoxy-L-thymidine's (telbivudine) use for the treatment of hepatitis B virus (HBV) is described in U.S. Pat. No. 6,395,716.

For administration to a pediatric population, a person with difficulties in swallowing or a renally impaired subject there is a need for an oral telbivudine solution.

An oral solution for aripiprazole is disclosed in Published US Patent Application No. 2002193438. However, these oral solutions are for the preparation of a sparingly soluble anti-schizophrenic compound and contain either lactic, acetic or tartic acid. Published International Application No. WO01/30318 provides an oral solution comprising galantamine in a non-buffered aqueous solution. However, an unbuffered aqueous solution would not guarantee that with time and storage conditions, the desired pH is maintained which would present a challenge for maintaining preservation of an oral solution. In addition, problems of bitterness of taste, stability of solution and microbial growth need to be overcome to prepare an oral telbivudine formulation. Disclosed herein is unexpected finding that specific preservative systems, aromatic types and concentrations, and solution pH can provide an oral telbivudine solution with pleasant taste, stability and retarded microbial growth.

SUMMARY OF THE DISCLOSURE

Provided herein is an oral solution comprising an effective amount of telbivudine or a pharmaceutically acceptable salt thereof. In some embodiments, the solution comprises a pharmaceutically suitable solvent system, at least one taste-enhancing/masking agent, a preservative system, and a buffer system. In another embodiment, the taste-enhancing/masking agent is able to mask the bitter taste of telbivudine.

In some of the above embodiments, the oral solution comprises up to 20 mg/mL or 50 mg/mL telbivudine.

In some of the above embodiments, the preservative system is a paraben or its respective salt, sorbic acid or its respective salts, or benzoic acid or its respective salts, preferably a paraben salt or benzoic acid.

In some of the above embodiments, the preservative system has a concentration range of 0.1-2.5 mg/mL.

In some of the above embodiments the oral solution is buffered with 1 N sodium hydroxide to a pH range of about 3 to about 5, e.g., a pH of about 4.0.

Provided herein is also an oral solution comprising 20 mg/mL telbivudine or a pharmaceutically acceptable salt thereof, 1.5 mg/mL benzoic acid, 0.2 mg/mL sodium saccharin, 1.0 mg/mL passion fruit, water and 9.6 mg/mL citrate acid anhydrous.

Provided herein is also an oral solution comprising 20 mg/mL telbivudine or a pharmaceutically acceptable salt thereof, 1.5 mg/mL benzoic acid, 0.2 mg/mL sodium saccharin, 1.0 mg/mL passion fruit, water and 9.6 mg/mL citrate acid anhydrous, at a pH of about 4.0.

Provided herein is also a method of treating a person with the oral solutions of the above embodiments. In some embodiments, the person is selected from the group consisting of a pediatric population, a person with difficulties in swallowing and a renally impaired subject.

DETAILED DESCRIPTION OF THE DISCLOSURE

During development of oral telbivudine formulations, it is found that a preserved system is not easily achievable, e.g., the pH of the solution must allow the activity of the selected preservative. Indeed, not all preservatives provide sufficient preservation at an acceptable pH for oral administration, especially against molds and yeasts (*Aspergillus niger* and *Candida albicans*). However, surprisingly, with a system containing benzoic acid at a pH of about 4, both preservation and drug stability may be achieved.

During pre-formulation, telbivudine stability is investigated within a range of pH from 2-9, at elevated temperature 50° C. It is demonstrated that a pH range from about 3-9 (for example, a pH range from about 4-9) is optimal for drug substance stability, i.e., from assay and thymine content (degradation product). The pH of the oral solution is a highly relevant parameter, due to the influence pH on the retardation of microbial growth in the solution during storage.

During development of oral telbivudine formulations there are problems of incorporating a flavor into the oral solution while maintaining telbivudine drug product stability. Specifically, to mask the slight bitter after taste of the telbivudine, a flavor is added to the oral solution. It is imperative to identify a soluble flavor which does not interfere with the telbivudine drug product. In addition, to obtain a clear telbivudine drug solution, the flavor should be used at a concentration that is completely miscible/soluble in the drug formulation.

Therefore, the present disclosure provides for a pharmaceutical solution suitable for oral administration comprising telbivudine, a pharmaceutically suitable solvent system, one or more taste-enhancing/masking agents, a preservative system, and a buffer system suitable to allow both drug stability and preservation, i.e., wherein said solution has a pH from about 3-5, e.g., from about 4-5. In one embodiment, the pH of the oral solution is 4.0+/−0.5.

The maximal concentration range of the telbivudine drug substance in the oral formulations disclosed herein is up to 50 mg/mL In one embodiment, the telbivudine drug substance in the final oral solution is 20 mg/ml.

The preservative system the oral formulations disclosed herein, such as parabens (e.g., including but not limited to butyl paraben, methlyparaben and propylparaben) and their salts, sorbic acid and salts, benzoic acid and salts could be used in a concentration range of 0.1-2.5 mg/mL.

The taste enhancing/masking agents can be a sweetener, for example, sodium saccharin, aspartame and/or a soluble flavor(s), such as passion fruit, strawberry, cherry flavors from Firmenich SA (Rue de la Bergère 7, CH 1217 Meyrin 2, Switzerland) in a concentration range of 0.05-0.5%. In one embodiment, the flavoring concentration is fixed at or below 0.1%. In yet another embodiment, 1 mg/ml passion fruit flavoring is used.

The buffer system can be, e.g., citrate buffer or phosphate buffer for a pH range of about 4-5, e.g., about 4+/−0.5. Citric acid provides a buffering system at an acidic pH and is stable and compatible with oral excipients. Citric acid also provides potential flavor enhancing effects and chelating effects on heavy metal ions (e.g., which could emanate from glass packaging).

The pharmaceutically suitable solvent system can be water, sorbitol syrup or ethanol. In the case of paraben preservative system, a suitable solvent system may include, e.g., propylene glycol.

Example 1

Exemplary Oral Formulations

The drug substance is dissolved and stabilized in an aqueous buffered, preserved and sweetened system. A preservation efficacy test (PET) is performed according to the procedure of Pharmacopeal procedures (e.g., Pharm. Eur.) The results and formulations are shown in Tables 1 and 2.

zoic acid at pH greater than about 5. Thus, the preservative benzoic acid in an oral telbivudine solution is most efficient at about pH 4, especially with regards to fungi growth.

Example 2

Exemplary Flavored Oral Formulations

The telbivudine drug substance is dissolved and stabilized in an aqueous buffered, preserved and flavored system. A final composition of a flavored telbivudine oral solution using benzoic acid as the single preservative is shown in Table 3. Although only a single preservative is used, surprisingly this formulation has a shelf life of at least 24 months. Furthermore, little benzoic acid decrease and little degradation of drug substance into thymine is observed over time for the Table 3 telbivudine formulation. Benzoic acid at 1.5 mg/mL is selected in order to decrease the likelihood of any advese reaction, e.g., in a pediatric population, while maintaining long term stability. The solution of Table 3 is effective in preservation against *E. Coli, P. Aeruginosa, A. Niger*, and *C. Albicans*. Additionally, in the Table 3 telbivudine formulation, passion fruit flavor remains stable, and all flavored solu-

TABLE 1

(Formulations and PET general results)

| Components | 46-1 | 46-2 | 172-1 | 172-2 | 50-1 | 50-2 | 175-1 | 175-2 |
|---|---|---|---|---|---|---|---|---|
| LDT600A | 20 mg | 20 mg | 20 mg | 20 mg | 20 mg | 20 mg | 20 mg | 20 mg |
| Methylparaben | 1.0 mg | 1.0 mg | | | | | | |
| Na-methylparaben | | | 1.0 mg | 1.0 mg | | | | |
| Propylparaben | 0.2 mg | 0.2 mg | | | | | | |
| Na-propylparaben | | | 0.2 mg | 0.2 mg | | | | |
| Benzoic acid | | | | | 1.5 mg | 1.5 mg | 2.0 mg | 2.0 mg |
| Propyleneglycol | 25 mg | 25 mg | | | | | | |
| Sodium saccharin | 0.2 mg | | 0.2 mg | 0.2 mg | 0.2 mg | | 0.2 mg | 0.2 mg |
| Aspartame | | 0.2 mg | | | | 0.2 mg | | |
| Citrate buffer 50 mM, pH 4.0 | | | ad. 1 mL | | | | ad. 1 mL | |
| Citrate buffer 50 mM, pH 5.0 | | | | ad. 1 mL | ad. 1 mL | ad. 1 mL | | ad. 1 mL |
| Citrate buffer 50 mM, pH 6.0 | ad. 1 mL | ad. 1 mL | | | | | | |
| PET | Not met | Not met | Met | Met | Not met | Not met | Met | Not met |

TABLE 2

(Formulations and PET specific results)

| Microbe | 46-1 | 46-2 | 50-1 | 50-2 | 172-1 | 172-2 | 175-1 | 175-2 |
|---|---|---|---|---|---|---|---|---|
| E. Coli | Met | Met | Met | Met | Met | Met | Met | Met |
| P. Aeruginosa | Met | Met | Met | Met | Met | Met | Met | Met |
| A. Niger | Met | Met | Met | Met | Met | Met | Met | Not Met |
| C. Albicans | Not Met | Not Met | Not Met | Not Met | Met | Met | Met | Met |

Interestingly, oral telbivudine solutions having either 2.0 mg/ml or 1.5 mg/ml benzoic acid, 0.02 mg/ml sodium saccharin and 20 mg/ml telbivudine in citric acid buffer of pH 5.0 did not meet the preservation efficacy criteria (solution preservation from microbes). This indicates the importance of pH regulation in the benzoic acid preservation system for telbivudine. Indeed, microbial limit test data shows microbial growth in oral telbivudine formulations preserved with bentions (i.e., cherry, strawberry and passion fruit) pass the PET test. However, when a strawberry flavor is used in place of passion fruit flavor, a component of the strawberry flavor degrades over 4 weeks at 50° C. Thus, the solution of Table 3 is considered most desirable—having the balanced properties of taste masking, drug substance stability, preservation against various organisms, and a long shelf life. The benzoic acid formulation also has a density close to water, making the solution easily mixable with a beverage if needed for administration, especially in the case of a pediatric population.

TABLE 3

| Components | Function | mg/mL |
|---|---|---|
| Telbivudine | Drug substance | 20 |
| Benzoic acid | Preservative | 1.5 |
| Sodium saccharin | Sweetener | 0.2 |
| Passion fruit | Flavor | 1.0 |
| Citrate acid anhydrous | Buffering system | 9.6 |
| Sodium hydroxide 1 N | Buffering system | ad pH 4.0 +/− 0.5 |
| Water | Solvent | ad 1 mL |

Interestingly, in one flavored oral solution containing 20 mg/ml telbivudine, two paraben preservatives (methyl and propylparaben), the preservative potassium sorbate (used against potential fungi and yeast growth) and a strawberry flavoring, there is a significant and surprising decrease of sorbic acid at accelerated conditions (i.e., to about 72% after 4 weeks at 50° C.). The same flavored oral paraben formulation containing passion fruit flavor displays a better sorbic acid assay at 50° C. after four weeks (about 90%). However, because of the surprisingly poor performance of the paraben flavored solutions in the sorbic acid assay, the requirement for more than one paraben preservative, the potential for paraben adverse reaction in a subject, and the undesirable taste of parabens, the single preservative benzoic acid solution of Table 3 is a superior formulation.

Example 3

Preparation of Oral Formulations

A minimal amount of water is heated up to 60-70° C., and then benzoic acid is added and stirred until a complete dissolution. The benzoic acid solution is cooled to room temperature and then each component is added and stirred until complete dissolution. Sodium hydroxide is then used to adjust the pH to about 3-5. Finally, the final volume is adjusted with water to the target volume.

Quantities of ingredients, represented by mg/mL pharmaceutical composition, used in Examples 1 and 2 are set forth in Tables 1 and 3, above.

What is claimed:

1. An oral solution comprising 20-50 mg/mL telbivudine or a pharmaceutically acceptable salt thereof, sodium saccharin, at least one soluble flavor, benzoic acid, and citrate buffer.

2. The oral solution according claim 1, wherein said oral solution is buffered to a pH range of about 4 to about 5.

3. The oral solution according to claim 1, wherein said sodium saccharin is present at 0.2 mg/ml.

4. The oral solution according to claim 1, wherein said soluble flavor is passion fruit flavor.

5. The oral solution according to claim 4, wherein said passion fruit flavor is present at 1.0 mg/ml.

6. The oral solution according to claim 1, wherein said benzoic acid is present at 1.5 mg/ml.

7. The oral solution according to claim 1, wherein said citrate buffer comprises 9.6 mg/ml citrate acid anhydrous.

8. An oral solution comprising 5 mg/ml telbivudine or a pharmaceutically acceptable salt thereof, 1.5 mg/ml benzoic acid, 0.2 mg/ml sodium saccharin, 1.0 mg/ml passion fruit flavor, and citrate buffer at pH 4.0+/−0.5.

9. An oral solution comprising 20-50 mg/ml telbivudine or a pharmaceutically acceptable salt thereof, sodium saccharin, at least one taste-enhancing/masking agent, sodium methylparaben, sodium propylparaben, and citrate buffer.

10. The oral solution according to claim 9, wherein said sodium methylparaben is present at 1.0 mg/ml and said sodium propylparaben is present at and 0.2 mg/ml.

11. The oral solution according claim 9, wherein said oral solution is buffered to a pH range of about 4 to about 5.

12. The oral solution according to claim 9, wherein said sodium saccharin is present at 0.2 mg/ml.

13. The oral solution according to claim 9, wherein said soluble flavor is passion fruit flavor.

14. The oral solution according to claim 13, wherein said passion fruit flavor is present at 1.0 mg/ml.

15. The oral solution according to claim 14, wherein said citrate buffer comprises 9.6 mg/ml citrate acid anhydrous.

* * * * *

UNITED STATES PATENT AND TRADEMARK OFFICE
CERTIFICATE OF CORRECTION

| | | |
|---|---|---|
| PATENT NO. | : 8,445,457 B2 | Page 1 of 1 |
| APPLICATION NO. | : 12/667975 | |
| DATED | : May 21, 2013 | |
| INVENTOR(S) | : Nabila Sekkat | |

It is certified that error appears in the above-identified patent and that said Letters Patent is hereby corrected as shown below:

In the Claims:

Column 6, lines 20-23, Claim 8 should read

8. An oral solution comprising ~~5~~ 20 mg/ml telbivudine or a pharmaceutically acceptable salt thereof, 1.5 mg/ml benzoic acid, 0.2 mg/ml sodium saccharin, 1.0 mg/ml passion fruit flavor, and citrate buffer at pH 4.0 +/-0.5.

Signed and Sealed this
Fifteenth Day of July, 2014

Michelle K. Lee
*Deputy Director of the United States Patent and Trademark Office*